United States Patent [19]

Schreiber

[11] 4,307,718
[45] Dec. 29, 1981

[54] VAPORIZER INTERLOCK

[75] Inventor: Peter J. Schreiber, Zionsville, Pa.

[73] Assignee: N.A.D. Inc., Telford, Pa.

[21] Appl. No.: 117,675

[22] Filed: Feb. 1, 1980

[51] Int. Cl.³ .............................................. A61M 11/00
[52] U.S. Cl. ...................... 128/200.19; 261/DIG. 65;
74/483 K; 137/637.1; 128/200.14
[58] Field of Search ...................... 128/200.11, 200.14,
128/200.16, 200.17, 200.19, 200.21, 203.12,
203.14, 203.25, 203.28, 204.13, 204.14;
261/DIG. 65; 74/483 K, 483 R; 137/637.1;
251/114, 116

[56] References Cited

U.S. PATENT DOCUMENTS

| | | | |
|---|---|---|---|
| 1,340,930 | 5/1920 | Catlin | 74/483RX |
| 2,633,933 | 4/1953 | Mueller | 137/637.1 |
| 2,646,474 | 7/1953 | Stratton | 74/483 R X |
| 2,764,182 | 9/1956 | Mitcham | 74/483 R X |

OTHER PUBLICATIONS

Ohio Medical Products, Unitrol Anesthesia Machine; Airco Catalog Form No. 9906 (Rev. 1978).
North American Drager, "Vapor Vaporizer".

*Primary Examiner*—Henry J. Recla
*Attorney, Agent, or Firm*—Caesar, Rivise, Bernstein & Cohen, Ltd.

[57] ABSTRACT

An interlock device for a pair of vaporizers of an anesthesia machine. Each vaporizer includes a rotary dial for establishing the vapor concentration provided. The interlock device insures that one vaporizer is closed whenever the other is open and comprises a pair of reciprocable pins and a cooperating pivotable lever. Each pin is arranged to be extended into a cam recess in the vaporizer dial by the pivoting action of the lever. Rotation of one dial automatically causes the pin located therein to move out of the cam recess and into contact with the lever. This action pivots the lever and causes it to contact the other pin to extend the other pin into the recess in the associated vaporizer dial, thereby locking the dial closed.

1 Claim, 4 Drawing Figures

VAPORIZER INTERLOCK

This invention relates generally to anesthesia machines and more particularly to interlock devices for anesthesia machine vaporizers.

Conventional anesthesia apparatus or machines commonly incorporate two separate vaporizers. Each vaporizer is arranged to dispense a metered amount of anesthesia vapor, e.g., Halothane, Enflurane, Methoxyflurane, etc., into the patient breathing circuit or fresh gas line.

While the construction of commercially available vaporizers varies from manufacturer to manufacturer, the most common type of vaporizer comprises a canister including a reservoir of the anesthesia, valve means and a rotatable dial coupled to the valve means for adjusting the valve means to establish the vaporizer concentration levels. For example, the VAPOR vaporizer used in anesthesia machines sold by North American Drager, the assignee of the instant invention, includes a rotary dial for adjusting the opening of a valve in the vaporizer to divide the gas flow in the vaporizer in accordance with the dial setting. Part of the gas flow passes through a by-pass, without entering the vaporizer chamber (where the anesthetic is located), while the remaining portion of the gas flow is lead through the vaporizer chamber for saturation by anesthesia vapor. The gas flow which is saturated with the vapor is then combined with the by-pass gas flow so that the whole amount of gas leaves the vaporizer at the set concentration. In the VAPOR vaporizer, the introduction of the gas with the anesthesia vapor into the fresh gas line is effected by an outlet valve under the control of a separate on/off switch. A pair of rotary cams and a pivoting lever are provided to serve as an interlock to insure that the outlet of the vaporizer is opened when the rotary dial is adjusted to any particular setting and to prevent the adjustment dial from being rotated to any setting when the on/off switch is closed, thereby precluding any gas from passing into the vaporization chamber when the outlet of the vaporizer is closed.

Irrespective of the type and construction of the vaporizers used in dual vaporizer anesthesia machines, it is desirable to provide means for preventing both vaporizers from being opened at the same time. Such action prevents an uptake of the vaporizing agent from one vaporizer into the other, which occurrence may have a detrimental effect on the patient.

Ohio Medical Products of Madison, Wisconsin, has recently offered a dual vaporizer anesthesia machine which incorporates a vaporizer interlock system to prevent simultaneous use of the two vaporizers. To that end, the interlock used in the Ohio Medical Products machine comprises a lever mounted behind the vaporizers and which is pivotable about its mid-point. The lever includes an engaging projection at one end adapted to engage a stop on the rotary dial of one vaporizer and a projection on the other end adapted to alternatively engage a similar stop on the other vaporizer dial. In operation, the lever is pivoted manually by the operator so that its projection engages the stop of the closed vaporizer to prevent the rotation of its concentration adjustment dial. This frees the projection at the other end of the lever from the associated stop of the other vaporizer dial, thereby enabling that vaporizer dial to be adjusted to any particular setting. In order to close the opened vaporizer and open the closed vaporizer to a particular setting, it is necessary to rotate the dial of the opened vaporizer until it is closed and thereafter pivot the lever so that its stop engages the stop of the now closed vaporizer, whereupon the other vaporizer, which had been locked closed, is unlocked and can be adjusted by the rotation of its dial.

While the Ohio Medical Products interlock device appears effective for insuring that both vaporizers are not opened at the same time, its mode of operation is not readily apparent from examination of the device and is, in fact, somewhat complex. In this regard, as noted heretofore, the operation of the device requires the manual rotation of the vaporizer adjustment dial coupled with the manual pivoting of the interlock lever.

Accordingly, it is the general object of the instant invention to provide an interlock system for vaporizers of an anesthesia machine which overcomes the disadvantages of the prior art.

It is a further object of the instant invention to provide an interlock for a pair of vaporizers which enables the setting of the concentration level for either vaporizer while locking the other vaporizer in the off position by the mere rotation of the concentration adjusting dial of the selected vaporizer.

It is a further object of the instant invention to provide an interlock for a pair of vaporizers in an anesthesia machine which is simple in construction and easy to use.

These and other objects of the instant invention are achieved by providing in an anesthesia machine having first and second vaporizers for introducing a metered concentration of vapor into a gas flow when opened, with each of said vaporizers comprising rotatable adjustment means for opening the vaporizer, establishing the vapor concentration introduced thereby, and closing the vaporizer, an improved interlock device. The interlock device is arranged for insuring that one of the vaporizers is closed whenever the other is opened and comprises pivotable lever means, first engagement means and second engagement means. The adjustment means of the first vaporizer includes first stop means and the adjustment means of the second vaporizer includes second stop means. The first engagement means is arranged for selective engagement with the first stop means while the second engagement means is arranged for selective engagement with the second stop means. The lever means and the first and second engagement means cooperate with each other so that when the adjustment means of the first and second vaporizers is closed, either of the first or second engagement means can be moved out of engagement with its associated stop means by the mere rotation of its associated adjustment means to open the vaporizer and establish any vapor concentration while the other engagement means is positioned in engagement with its associated stop means to lock its associated adjustment means closed.

Other objects and many of the attendant advantages of this invention will be readily appreciated as the same becomes better understood by reference to the following detailed description when considered in connection with the accompanying drawings wherein.

Figure 1:
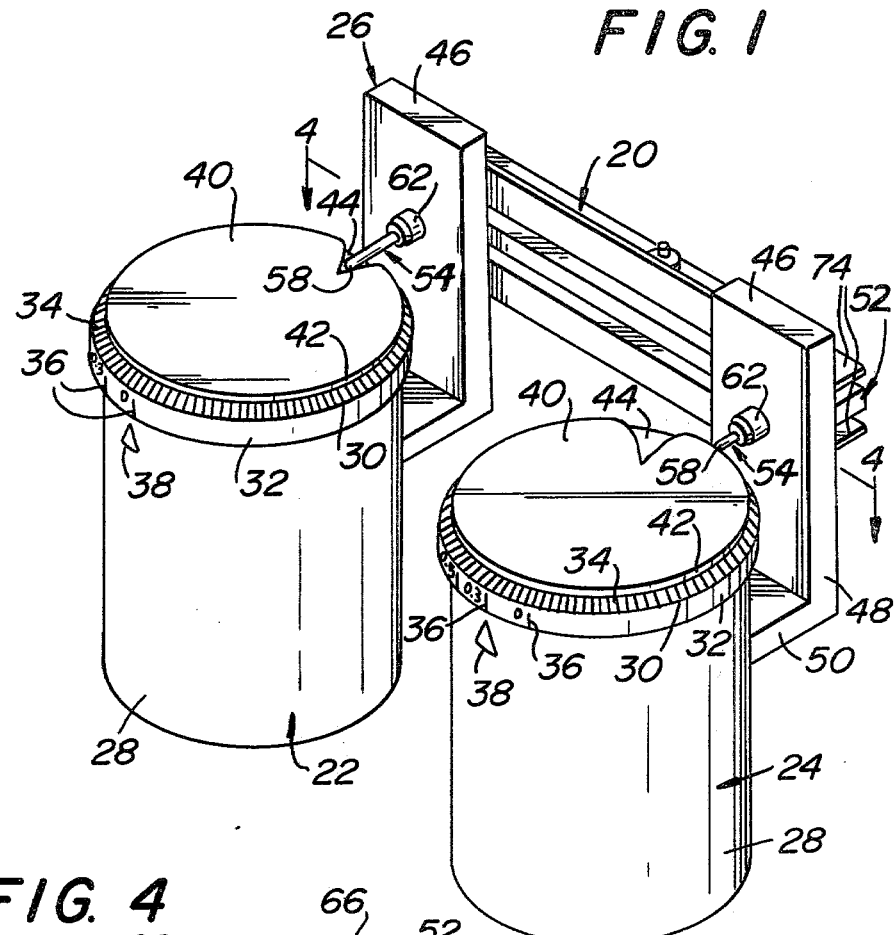
FIG. 1 is a front elevational view of a portion of an anesthesia machine showing the vaporizer interlock device of the instant invention used in conjunction with a pair of vaporizers.

Referring now to FIG. 1, wherein like reference characters refer to like parts, there is shown generally at 20 an interlock device for use with a pair of vaporizers 22 and 24 of a conventional anesthesia machine, a portion of which is shown by the reference numeral 26.

Each of the vaporizers 22 and 24 is of conventional internal construction save for the use of a respective camming member, to be described in considerable detail later, coupled to the vapor concentration adjustment dial. Each vaporizer comprises a canister 28 containing the anesthesia vapor to be dispensed and the means for metering the same into the gas line of the machine 26. The concentration of the anesthesia vapor provided by each of the vaporizers is determined by the setting of the vapor concentration adjusting dial 30. As can be seen, each dial 30 is a generally disk-shaped member having a circular, outer surface 32 whose upper edge is tapered and is ribbed to provide a manual gripping surface 34. The outer surfaces 32 include plural indicia 36 engraved thereon corresponding to the vapor concentration provided by the vaporizer. The canister 28 includes an arrow or pointer indicia 38 to indicate the particular vapor concentration setting as established by the vaporizer. When the zero mark of indicia 36 is aligned with the arrow 38, the vaporizer is closed. The rotation of the dial 30 counter-clockwise opens the vaporizer to introduce vaporized gas into patient breathing circuit (not shown). The concentration level established by the setting of the dial 30 is displayed by the indicium 36 disposed opposite to pointer 38.

As noted heretofore, the dial 30 of each vaporizer includes a respective camming member. This member is shown by the reference numeral 40 and is in the form of a disk having a circular cam surface 42 which is concentric with the dial surface 32. Each of the camming members 40 includes a respective notch 44 in its circular, peripheral surface 42. The notches 44 will be described in considerable detail later. It will suffice for now to say that each notch forms an inclined cam surface which is arranged to cooperate with a portion of the interlock 20 to preclude the opening of one vaporizer if the other vaporizer is in any position other than the fully closed or off position.

Each of the vaporizers is mounted on a portion of the anesthesia machine, such as the console (not shown) by a respective L-shaped mounting bracket 46. Each bracket includes a downwardly extending section 48 and a horizontal portion 50. The cannister 28 of the vaporizer is connected to portion 50 of the bracket.

The interlock device 20 basically comprises pivotable lever means 52 (FIG. 1) and an associated pair of engagement means in the form of a pair of cam follower pins 54. Each of the cam follower pins is arranged for reciprocation into or out of a respective cam recess 44 in the dial of an associated vaporizer.

As can be seen clearly in FIG. 1, each of the cam recesses 44 is in the form of a right angle, V-shaped, slot so that the sides of the slot incline upward. The upward inclined sides of the slot form inclined cam surfaces 56. Each of the engagement pins 54 is an elongated rod-shaped member having opposed rounded ends 58 and 60. The rounded end 58 of the pin serves as the cam following surface of the pin and is adapted to ride along the periphery of the cam means 40.

Each of the cam follower pins extends horizontally through a sleeve 62 located in the portion 48 of bracket 46. Each pin is freely reciprocable longitudinally within said sleeve. The pivoting lever 52 is in the form of an elongated bar which is arranged to be pivoted about a vertical pivot pin 64 in either the clockwise or counter-clockwise direction (as shown by the double headed arrow 66 in FIG. 4). The bar is located with respect to the cam follower pins 54 so that when pivoted clockwise one end of the pivot bar 52 engages the rounded end 60 of one pin and when pivoted counter-clockwise the opposed end of the bar engages the corresponding end of the other pin.

Figure 2:
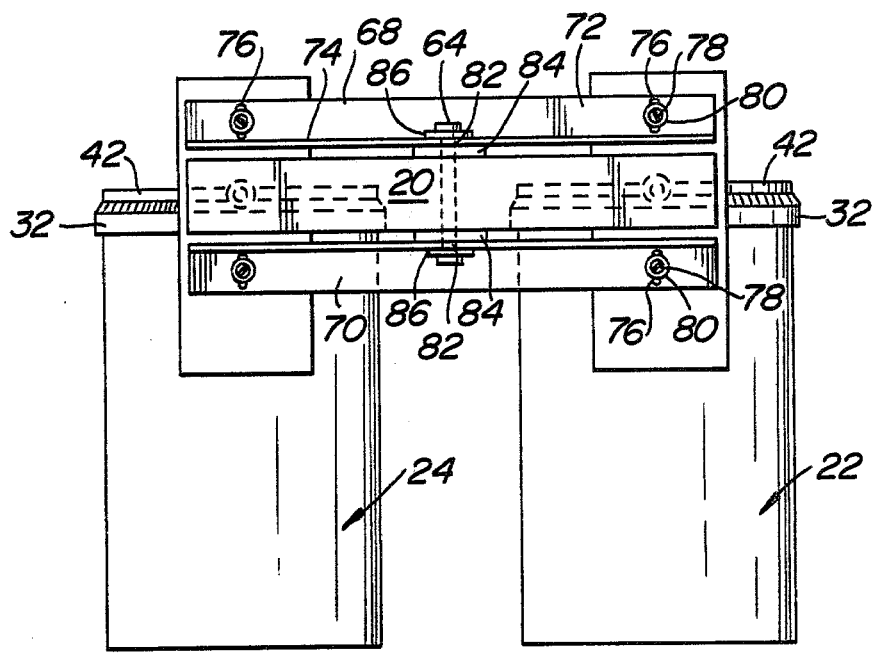
FIG. 2 is a rear elevational view of the portion of the anesthesia machine shown in FIG. 1.
Figure 3:
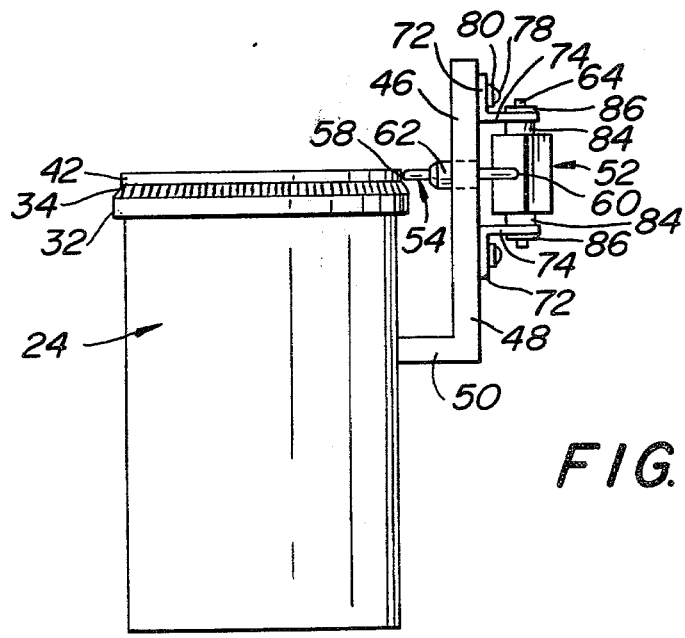
FIG. 3 is a side elevational view of the portion of the anesthesia machine shown in FIGS. 1 and 2.

The bar is mounted between a pair of support flanges 68 and 70 (FIG. 2). Each flange is an elongated L-shaped member which includes a vertically extending portion 72 and a horizontal flange 74. A pair of vertically oriented elongated slots 76 are located within the portion 72 of the flange adjacent the respective ends thereof. A respective threaded fastener, such as screw 78 extends through the slot and into an associated threaded opening in the portion 48 of the bracket 46. A washer 80 is located under the screw head. The lower support flange is mounted in an identical manner to the upper support flange. A vertical pivot pin 64 extends through aligned openings 82 in the upper and lower support flanges 68 and 70, respectively. The pivot bar 52 is disposed horizontally between the upper and lower support flanges and is centered, via a pair of washers 84. The pivot pin is held in place by a pair of locking C-rings 86 located in respective annular recesses (not shown) in the periphery of the pin adjacent each end.

Each of the cam recesses 44 is located on the periphery of the camming means 40 so that it is aligned with its associated cam following pin 54 when the vaporizer is closed (at which time the zero indicium 36 is aligned with the pointer indicium 38).

Figure 4:
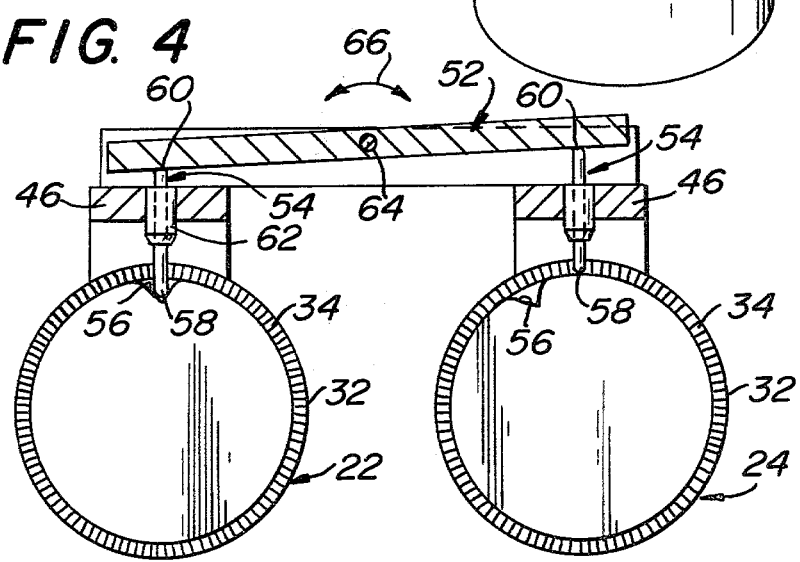
FIG. 4 is a sectional view taken along line 4—4 of FIG. 1.

Each of the cam follower pins 54 is arranged for selective engagement with its associated cam recess 44. The lever 52 and the cam follower pins cooperate with each other so that when the vapor concentration dial 30 of either vaporizer 22 or 24 is closed, the cam follower pin associated with the other vaporizer can be moved out of the cam recess 44 by the mere rotation of the dial. For example, as the dial 30 of vaporizer 24 is rotated to establish a desired vapor concentration setting, the end surface 58 of the cam following pin associated therewith rides up the inclined surface 56 of the cam recess until it is on the circular periphery 42. This action moves the cam follower pin to the rear, i.e., toward the lever 52, whereupon its rear surface 60 engages the lever 52 to pivot the lever in the counter-clockwise direction as seen in FIG. 4. The counter-clockwise pivoting of lever 52 causes a portion of its opposite end to engage the end 60 of the other cam follower pin 54, thereby forcing that pin forward, i.e., toward the vaporizer 22 and firmly into the aligned cam recess 44 in its camming means 40. The cam recess thus acts as a stop to lock the vaporizer 22 in the closed position.

In the event it is desired to close vaporizer 24 and open vaporizer 22, all that is required is to manually grasp the dial of vaporizer 24 to rotate it in the clockwise direction until the vaporizer is closed, whereupon its cam recess 44 is aligned with its associated cam follower pin 54. The vapor concentration dial of vaporizer 22 is then manually rotated in the clockwise direction, whereupon the cam follower surface 58 of the associated pin rides up the inclined surface 56 and onto the circular cam surface 42. This action causes the pin 54 to move to the rear, thus engaging the end of lever 52 to cause the lever to pivot in the clockwise direction. The clockwise pivoting of lever 52 causes its opposed end to force the other cam follower pin 54 forward, that is, into the aligned cam recess 44 of vaporizer 24. So long as the vaporizer 22 is at any concentration setting other that the zero (closed) setting, the cam follower pin 54 associated therewith will hold the lever in the clockwise pivoted position so that the associated cam follower pin is locked within the cam recess 44 in the dial of vaporizer 24.

As will be appreciated from the foregoing, the interlock device 20 of the instant invention is simple in construction and extremely effective in operation. In this regard, all that is required to effect the adjustment of one vaporizer and the locking of the other vaporizer in the closed position is the mere rotation of the vaporizer concentration adjusting dials. The cam surface of the dial of the opened vaporizer effectuates the pivoting action of the lever means to lock the other vaporizer closed without requiring the operator to grasp the lever to pivot it to the locked position. This feature is of considerable importance since it simplifies operating procedure, thereby minimizing the chance of operator error.

Without further elaboration, the foregoing will so fully illustrate my invention that others may, be applying current or future knowledge, readily adapt the same for use under various conditions of service.

What is claimed as the invention is:

1. In an anesthesia machine having first and second vaporizers mounted in side-by-side relation, each arranged for introducing a metered concentration of vapor into a gas flow when opened, each of said vaporizers comprising rotatable adjustment means having a dial for opening said vaporizer, establishing the vapor concentration introduced thereby and closing said vaporizer, said vapor concentration being adjustable by said rotatable adjustment means, the improvement comprising an interlock device for insuring that one of said vaporizers is closed whenever the other is opened, said device comprising a respective cam surface on each of said dials, bracket means mounted on said anesthesia machine, pivotable lever means pivotably mounted on said bracket means, first engagement means, and second engagement means, each of said cam surfaces including a recess having an inclined surface, the recess of said first vaporizer forming first stop means, the recess of said second vaporizer forming second stop means, said first engagement means comprising a cam follower pin separate from said lever means and slidably mounted on said bracket means such as to slide along the cam surface of the first vaporizer dial as said dial is rotated and to selectively engage said first stop means by reciprocation into and out of the recess thereof, said second engagement means comprising a cam follower pin separate from said lever means and slidably mounted on said bracket means such as to slide along the cam surface of the second vaporizer dial as said dial is rotated and to selectively engage said second stop means by reciprocation into and out of the recess thereof, said lever means comprising an elongated member pivotably mounted on said bracket means for pivoting about an intermediate point of said lever means, one of said cam follower pins engaging the lever means at any point on one side of said intermediate point and with the other of said cam follower pins engaging the lever means at any point on the opposite side of said intermediate point, each of said cam follower pins being slidably mounted on said bracket means between the engaging points on said lever means and the dial of the associated vaporizer, said lever means and said pins of said first and second engagement means cooperating with each other so that when the adjustment means of said first and second vaporizer are closed one or the other of said first and second engagement means can be automatically moved out of engagement with its associated stop means by rotating its associated dial, whereupon the associated cam follower pin slides along the dial's inclined surface and out of its recess to open the vaporizer and establish any vapor concentration while pivoting said lever about said intermediate point so that said lever engages the cam follower pin of the other engagement means to automatically move said pin into the recess in the dial of the associated vaporizer to lock the adjustment means thereof closed.

* * * * *